United States Patent [19]

Tentorio

[11] Patent Number: 5,144,025
[45] Date of Patent: Sep. 1, 1992

[54] PROCESS FOR THE RESOLUTION OF INTERMEDIATES USEFUL IN THE PREPARATION OF 1,5-BENZOTHIAZEPINES

[75] Inventor: Dario Tentorio, Vigano', Italy

[73] Assignee: Zambon Group S.p.A., Vicenza, Italy

[21] Appl. No.: 504,860

[22] Filed: Apr. 5, 1990

[30] Foreign Application Priority Data

Apr. 2, 1990 [IT] Italy ................ 20134 A/89

[51] Int. Cl.$^5$ .......................................... C07D 281/10
[52] U.S. Cl. ........................................ 540/491; 560/17
[58] Field of Search ............................ 540/491; 560/17

[56] References Cited

U.S. PATENT DOCUMENTS

| | | | |
|---|---|---|---|
| 4,963,671 | 10/1990 | Krapcho | 540/491 |
| 5,055,464 | 10/1991 | Murakami et al. | 540/491 |

FOREIGN PATENT DOCUMENTS

| | | | |
|---|---|---|---|
| 0098892 | 1/1984 | European Pat. Off. | 540/491 |
| 0127882 | 12/1984 | European Pat. Off. | 540/491 |
| 0158340 | 10/1985 | European Pat. Off. | 540/491 |
| 1236467 | 6/1971 | United Kingdom | 540/491 |
| 2130578 | 6/1984 | United Kingdom | 540/491 |
| 2167063 | 5/1986 | United Kingdom | 540/491 |

OTHER PUBLICATIONS

Fieser and Fieser "Organic Chemistry" 3rd Ed. (1958) pp. 269–273.

Merck Index (X) #3189.
Merck Index (X) #8943.
Merck Index (X) #8945.
Chemical Abstracts, vol. 84, No. 21, Abs. 15093m, Clark, J. C. et al, "Resolution of Esters of Phenylglycine with" . . . (1976).
Chemical Abstracts, vol. 88, No. 9, Abs. 62611a, Sumitomo Chem. Co. Ltd. "D-threo-p-(Methylsulfonyl)phenylserine esters" (1978).

Primary Examiner—Robert T. Bond
Attorney, Agent, or Firm—Stevens, Davis, Miller & Mosher

[57] ABSTRACT

A process for the resolution of amminoesters of the formula

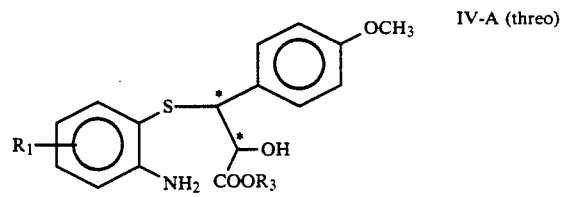

IV-A (threo)

wherein $R_1$ and $R_3$ have the meanings reported in the specification, by tartaric acid and analogs thereof, is described. The compounds of formula IV-A are intermediates useful in the preparation of optically active (2-(4-methoxyphenyl)-1,5-benzothiazepin-4(5H)ones.

10 Claims, No Drawings

PROCESS FOR THE RESOLUTION OF INTERMEDIATES USEFUL IN THE PREPARATION OF 1,5-BENZOTHIAZEPINES

The present invention concerns a process for the resolution of aminoesters by tartaric acid and analogs thereof and, more particularly, it concerns a process for the resolution of aminoesters useful as intermediates in the synthesis of optically active 2-(4-methoxyphenyl)-1,5-benzothiazepin-4(5H)ones of formula

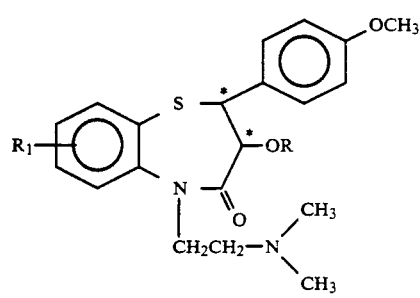

wherein
R represents a hydrogen atom or acetyl,
$R_1$ represents a hydrogen atom or chlorine atom,
the asterisks mark the asymmetric carbon atoms.

Specific examples of the compounds of formula I are Diltiazem, (+)-(2S,3S)-3-acetoxy-5-[2-(dimethylamino)-ethyl]-2,3-dihydro-2-(4-methoxyphenyl)-1,5-benzothiazepin-4(5H)-one (Merck Index, X Ed., No. 3189, page 466) and TA-3090, (+)-(2S,3S)-3-acetoxy-8-chloro-5-[2-(dimethylamino)-ethyl]-2,3-dihydro-2-(4-methoxyphenyl)-1,5-benzothiazepin-4(5H)-one (Annual Drug Data Report 1987, page 507). Various methods for the preparation of the compounds of formula I are known in the literature such as for example those described in British patent No. 1,236,467, in European patent applications No. 127,882 and No. 158,340 and in the British patent application No. 2,167,063 all in the name of Tanabe Seiyaku Co. Ltd.

Most of these methods substantially foresee the following reaction scheme.

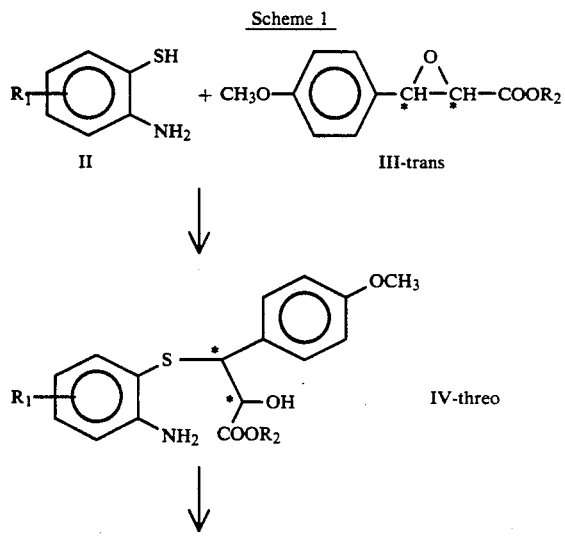

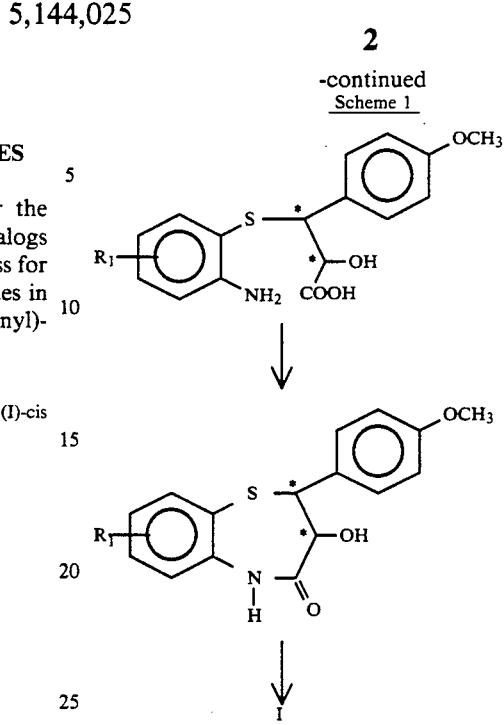

wherein $R_1$ represents a hydrogen or chlorine atom, $R_2$ represents a lower alkyl and the asterisks mark the asymmetric carbon atoms.

Each of these methods necessarily foresee an optical resolution step, generally at the level of an intermediate of the synthesis, in order to separate the (2S,3S) from the (2R,3R) enantiomer.

In fact, there are known the resolution of the cyclic intermediate of formula VI by 1-(2-naphthylsulphonyl)-pyrrolidine-2-carbonyl chloride described in the above cited British patent application No. 2,167,063 and the resolution of the intermediate of formula V by optically active bases such as 4-hydroxyphenyl-glycine methyl ester and cinchonidine described in the above cited European patent application No. 127,882; by alpha-phenethylamine described in the European patent No. 98,892 (Tanabe Seiyaku Co. Ltd.) and by L-lysine described in the British patent application No. 2,130,578 (Istituto Luso Farmaco).

To our knowledge, resolution processes at the level of the intermediate of formula IV have never been described.

We have now found that the intermediate aminoesters of formula IV may be conveniently resolved in the two enantiomers (2S,3S) and (2R,3R) by using optically active tartaric acid or analogs thereof such as ethers or esters of the two hydroxy groups, as resolving agents.

Thus, object of the present invention is a process for the resolution of the compounds of formula

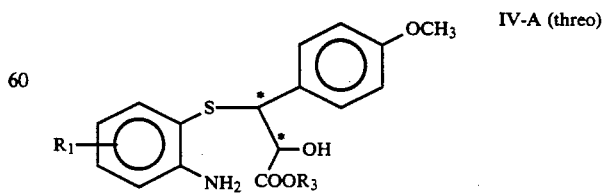

wherein
$R_1$ represents a hydrogen or chlorine atom,
$R_3$ represents a $C_1$–$C_3$ alkyl, preferably methyl, the asterisks mark the asymmetric carbon atoms; which process comprises the treatment of the racemic mixture of the compound of formula IV-A with optically active tartaric acid or analogs thereof in a suitable organic solvent, the separation of the diastereoisomeric salts of compound IV-A with optically active tartaric acid or analogs thereof, and optionally the liberation thereof to obtain the single enantiomers of the compounds of formula IV-A.

By the expression optically active tartaric acid we mean (2R,3R) and (2S,3S)-2,3-dihydroxy-1,4-butanedioic acid, i.e. (2R,3R) and (2S,3S)-tartaric acid.

Specific examples of tartaric acid analogs as above defined, i.e. ethers or esters of the two hydroxy groups are (2R,3R)-2,3-dimethoxy-1,4-butanedioic acid, (2R,3R)-2,3-diacetoxy-1,4-butanedioic acid and their (2S,3S) enantiomers.

Herein after by the expression tartaric acid we make reference to both tartaric acid and analogs thereof as above defined.

The racemic mixture of the aminoester of formula IV-A is treated with optically active tartaric acid, i.e. with tartaric acid having configuration R,R or S,S, in a suitable solvent in order to obtain the corresponding diastereoisomeric salts.

The molar ratio of the aminoester IV-A and tartaric acid is comprised between 0.5 and 3, preferably between 0.8 and 1.5.

Suitable solvents are lower alkanecarboxylic acids such as acetic or propionic acid, optionally in admixture with small amounts of water.

The water optionally present in the mixture is in a concentration up to 8% weight/volume, preferably between 1.5 and 3.5%.

The two diastereomeric salts of compound IV-A with tartaric acid are separated by crystallization according to conventional procedures.

Depending on the kind of tartaric acid used, (R,R) or (S,S), one of the two diastereomeric salts separates and is isolated by filtration.

From the remaining solution the other isomer may be recovered too. The liberation of the diastereomeric salts thus separated allows to obtain the optically active compounds of formula IV-A having an optical purity generally higher than 85-90%.

The enantiomerically pure aminoesters of formula IV-A, with optical purity higher than 99% may be obtained by crystallization of the diastereomerically enriched mixture of the salt of aminoester IV-A with tartaric acid or by crystallization of the enantiomerically enriched aminoester itself.

It is worth noting that the preparation of the enantiomerically pure aminoesters IV-A by crystallization starting from an enriched mixture of aminoester IV-A may be carried out by using an enriched mixture from whatever origin and therefore it is not restricted to the mixture obtained by the resolution process object of the invention.

Thus, a second object of the present invention is a process for the preparation of an enantiomerically pure aminoester IV-A by crystallization in a suitable solvent of a mixture enriched in the same enantiomer.

Thus, for example, starting from a mixture enriched in one enantiomer coming from the mother liquors from which the salt with tartaric acid of the other enantiomer was separated, it is possible by a simple crystallization to obtain the first enantiomer in pure form.

Suitable solvents for the crystallization are lower alcohols, lower alkanecarboxylic acids or chlorinated hydrocarbons optionally in mixture with small amounts of water (e.g., 1-4% w/v).

This crystallization method object of the present invention allows, in particular, to obtain the aminoester IV-A enantiomerically pure starting from a mixture of diastereomer salts with a d.e. (diastereomeric excess)≧60% as well as starting from an enantiomeric mixture with an e.e. (enantiomeric excess)≧60%.

It is important to underline that by the resolution process object of the present invention it is possible to obtain the enantiomers of the compounds IV-A in good yields and high productivity.

The process object of the invention allows also the recovery of tartaric acid used as resolution agent that can be thus reutilized in a subsequent resolution cycle.

The optically active aminoester IV-A obtained by the process object of the present invention may be than transformed into the corresponding 2-(4-methoxyphenyl)-1,5-benzothiazepin-4(5H)one of formula I, for example by following the synthesis process reported in scheme 1.

Alternatively, it is clear for the expert in the field that the resolution at the level of intermediate IV-A allows to avoid the transformation into the corresponding acid of formula V and therefore allows to carry out the cyclization reaction directly on the optically active aminoester IV-A.

The cyclization is carried out by heating the resolved compound IV-A preferably in the presence of a solvent such as xilene or toluene and of small amounts of an acid, e.g. p.toluensulphonic acid.

A preferred embodiment of the invention is the process having the aim of preparing the esters of 2-hydroxy-3-(2-aminophenylthio)-3-(4-methoxyphenyl)-propionic acid (IV-A, $R_1$=H) useful intermediates for the preparation of Diltiazem.

By a practical point of view, the realization of the process object of the invention, in a preferred embodiment, is the following.

The aminoester of formula IV-A ($R_1$=H), preferably the methyl ester, in racemic form and optically active tartaric acid are added to a mixture of an alkanecarboxylic acid, preferably acetic acid, and water.

The diastereomeric salt of the aminoester IV-A ($R_1$=H) with tartaric acid is separated.

By using tartaric acid with S,S configuration, i.e. the not-natural tartaric acid (Merck Index, X Ed., No. 8943, page 1302) the salt of the aminoester having 2S,3S configuration is separated, the enantiomer having configuration corresponding to that of Diltiazem which is collected by a simple filtration.

The aminoester (2S,3S) of formula IV-A ($R_1$=H) is then liberated from the salt by treatment with water or a polar organic solvent. Example of polar organic solvents are lower alcohols, lower alkanecarboxylic acids, chlorinated hydrocarbons.

By using natural tartaric acid with R,R-configuration (Merck Index, X Ed., No. 8945, page 1303) the salt of the aminoester having configuration 2R,3R is separated.

After separation by simple filtration of the diastereomeric salt, the aminoester IV-A ($R_1$=H) having desired configuration 2S,3S is obtained from the resulting solution by simple evaporation of the solvent and treatment with water or a polar organic solvent.

Optionally, the optically active aminoester thus obtained may be further purified by crystallization.

Preferred crystallization solvents are isopropyl alcohol, acetic acid or methylene chloride.

From the mother liquors of the crystallization is further possible to recover the racemic product possibly present thus allowing its use in a subsequent resolution process.

As above underlined, the process object of the present invention represents an extremely advantageous process, simple and unexpensive, for the preparation of the compounds of formula I.

By a practical point of view, the process object of the invention allows, in fact, to carry out the resolution at the level of the first synthetic intermediate, to avoid the subsequent hydrolysis of the aminoester, reported in scheme 1, by carrying out the cyclization directly on the aminoester, to recover both the non-resolved aminoester IV-A and that having the undesired configuration and the resolving agent. The recovered unresolved aminoester and the resolving agent may be re-used directly in a subsequent resolution step.

The aminoester having the undesired configuration may be optionally re-used too, after racemization.

With the aim to better illustrate the present invention the following example are given.

EXAMPLE 1

Resolution of methyl threo-2-hydroxy-3-(2-aminophenylthio)-3-(4-methoxyphenyl)-propionate with (2R,3R) tartaric acid Acetic acid (125 ml), water (2 ml) and (2R,3R) tartaric acid (17 g; 0.113 mol) were charged into a 500 ml reactor.

The mixture was kept under stirring and heated up to 90° C. and then left at this temperature for 15 minutes.

The obtained solution was cooled at 70° C.

The racemic methyl threo-2-hydroxy-3-(2-aminophenylthio)-3-(4-methoxyphenyl)-propionate (50 g; 0.15 mol) was added.

During the addition the temperature spontaneously decreased to +50° C. At this temperature the enantiomerically pure salt of methyl 2-hydroxy-3-(2-aminophenylthio)-3-(4-methoxyphenyl)propionate with (2R,3R) tartaric acid (200 mg) was seeded.

During 1.5 hour it was cooled up to 25° C. under stirring and it was left at this temperature for 3 hours. The insoluble was filtered and washed with methylene chloride (70 ml).

The organic layer was collected into the acetic mother liquors. The product was suspended, under stirring, in a mixture containing water (70 ml) and methylene chloride (70 ml) up to the formation of two limpid phases.

Alternatively, the phases were separated and the acqueous phase was extracted with methylene chloride (70 ml).

The methylene extraction phases were collected and concentrated to dryness to obtain methyl (2R,3R)-2-hydroxy-3-(2-aminophenylthio)-3-(4-methoxyphenyl)-propionate (19.3 g—77.2% yield) with $[\alpha]_D^{20} = -95.5°$ (c=0.5% in CHCl$_3$).

The acetic mother liquors were reunited with the methylene chloride washing and concetrated under vacuum (about 15 mmHg) at 35° C. up to residue. The residue was suspended under stirring into a mixture containing water (70 ml) and methylene chloride (70 ml).

Alternatively the residue can be crystallized by isopropanol (300 ml) to give the enantiomerically pure methyl (2S,3S)-2-hydroxy-3-(2-aminophenylthio)-3-(4-methoxyphenyl)-propionate with 70% yield; $[\alpha]_D^{20} = +100°$ (c=0.5% in CHCl$_3$).

The phases were separated and the acqueous phase was extracted with methylene chloride (70 ml).

The collected organic phases were concentrated to obtain the crude methyl (2S,3S)-2-hydroxy-3-(2-aminophenylthio)-3-(4-methoxyphenyl)propionate (30.7 g; $[\alpha]_D^{20} = +58.4°$).

The crude so obtained was suspended under stirring in isopropanol (300 ml).

The suspension was heated at 60° C. until complete solution and then cooled at 30° C. in one hour.

The suspension was maintained under stirring at 30° C. for one hour and then filtered to obtain, after drying under vacuum, methyl (2S,3S)-2-hydroxy-3-(2-aminophenylthio)-3-(4-methoxyphenyl)propionate (19.4 g; 78% yield with $[\alpha]_D^{20} = +97.9°$ (c=0.5% in CHCl$_3$).

The isopropanol mother liquors were concentrated up to a solid residue obtaining the racemic methyl threo-2-hydroxy-3-(2-aminophenylthio)-3-(4-methoxyphenyl)propionate (10 g).

The acqueous phases were collected and concentrated to dryness to obtain (2R,3R) tartaric acid (17 g) with $[\alpha]_D^{20} = +12°$ (c=20%, H$_2$O) and 96% acidimetric titre.

EXAMPLE 2

Resolution of methyl threo-2-hydroxy-3-(2-aminophenylthio)-3-(4-methoxyphenyl)-propionate with (2S,3S) tartaric acid Acetic acid (125 ml), water (2 ml) and (2S,3S) tartaric acid (17.6 g; 0.117 mol) were charged into a 500 ml reactor.

The mixture was kept under stirring and heated up to 90° C. and then left at this temperature for 15 minutes. The obtained solution was cooled at 70° C.

The racemic methyl threo-2-hydroxy-3-(2-aminophenylthio)-3-(4-methoxyphenyl)-propionate (50 g; 0.15 mol) was added.

During the addition the temperature spontaneuosly decreased to +50° C.

At this temperature the enantiomerically pure salt of methyl 2-hydroxy-3-(2-aminophenylthio)-3-(4-methoxyphenyl)propionate with (2S,3S) tartaric acid (200 mg) was seeded.

During 1.5 hour it was cooled up to 25° C. under stirring and it was left at this temperature for 3 hours.

The insoluble was filtered and washed with methylene chloride (70 ml).

The product was suspended, under stirring, in a mixture containing water (70 ml) and methylene chloride (70 ml) up to the formation of two limpid phases.

The phases were separated and the acqueous phase was extracted with methylene chloride (70 ml).

The methylene phases were collected and concentrated to dryness for obtaining methyl (2S,3S)-2-hydroxy-3-(2-aminophenylthio)-3-(4-methoxyphenyl)-propionate (19.3 g—77.2% yield) with $[\alpha]_D^{20} = -95.5°$ (c=0.5% in CHCl$_3$).

By working in a way analogous to that described in example 2 the following resolutions with (2S,3S) tartaric acid were carried out.

TABLE 1

Resolution with (2S, 3S) tartaric acid of racemic methyl threo-2-hydroxy-3-(2-aminophenylthio)-3-(4-methoxyphenyl)propionate (50 g; 0.15 mol).

| Example | Solvent (ml) | Tartaric acid (g) | Yield (g) | $[\alpha]_D^{20}$ |
|---|---|---|---|---|
| 3 | $CH_3COOH/H_2O$ (110/2) | 12.5 (0.083 mol) | 18.4 | +89.4° |
| 4 | $CH_3COOH/H_2O$ (125/2) | 17.6 (0.117 mol) | 20.5 | +86.1° |
| 5 | $CH_3COOH/H_2O$ (120/4) | 17.6 (0.117 mol) | 17.0 | +95.7° |
| 6 | $CH_3COOH$ (130) | 17.6 (0.117 mol) | 20.8 | +88.0° |
| 7 | $CH_3COOH$ (180) | 22.5 (0.15 mol) | 16 | +95.6° |
| 8 | $CH_3CH_2COOH/H_2O$ (200/10) | 17.0 (0.113 mol) | 19 | +87.6° |
| 9 | $CH_3COOH/H_2O$ (120/10) | 17.0 (0.113 mol) | 13.6 | +92.9° |

EXAMPLE 10

Cyclization of methyl (2S,3S)-2-hydroxy-3-(2-aminophenylthio)-3-(4-methoxyphenyl)propionate To a suspension of methyl (2S,3S)-2-hydroxy-3-(2-aminophenylthio)-3-(4-methoxyphenyl)propionate (19.4 g; 0.058 mol), prepared as described in example 1, in xylene (223 ml), monohydrate p.toluene-sulfonic acid (1.1 g) was added.

The mixture was heated to reflux under stirring for 5 hours. Then it was cooled and the insoluble was filtered and dried in an oven under vacuum at 70° C. to give (2S,3S)-2,3-dihydro-3-hydroxy-2-(4-methoxyphenyl)-1,5-benzothiazepin-4(5H)-one (16.1 g—90% yield) with titre 98% weight/weight.

What we claim is:

1. A process for the preparation of the compounds of formula

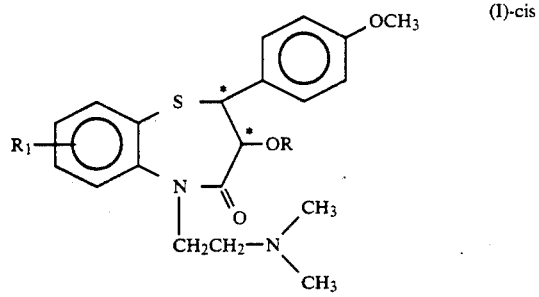

wherein

R represents a hydrogen atom or acetyl, $R_1$ represents a hydrogen atom or chlorine atom, the asterisks mark the asymmetric carbon atoms; which comprises the treatment of a racemic mixture of a compound of formula

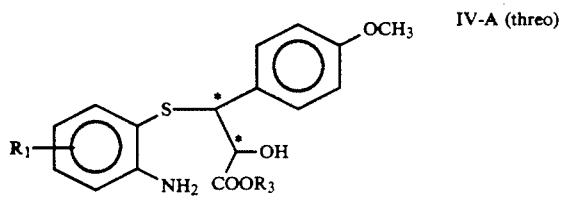

wherein $R_1$ represents a hydrogen or chlorine atom, $R_3$ represents a $C_1-C_3$ alkyl, the asterisks mark the asymmetric carbon atoms; with optically active tartaric acid or analogs thereof in a suitable organic solvent, the separation of the diastereoisomeric salts of compound IV-A with optically active tartaric acid or analogs thereof, the optional liberation of the salts and the crystallization in a suitable solvent of the enantiomerically enriched mixture thus obtained.

2. A process according to claim 1 wherein $R_3$ is methyl.

3. A process according to claim 1 wherein the molar ratio of the aminoester IV-A and tartaric acid or analogs thereof is comprised between 0.5 and 3.

4. A process according to claim 1 wherein the optically active tartaric acid is (R,R) or (S,S)-tartaric acid.

5. A process according to claim 1 wherein the organic solvent is a lower alkanecarboxylic acid optionally in admixture with small amounts of water.

6. A process according to claim 1 wherein the solvent for the crystallization of the enantiomerically enriched mixture is selected among lower alcohols, lower alkanecarboxylic acids, chlorinated hydrocarbons optionally in the presence of small amounts of water.

7. A process for the resolution of compounds of formula

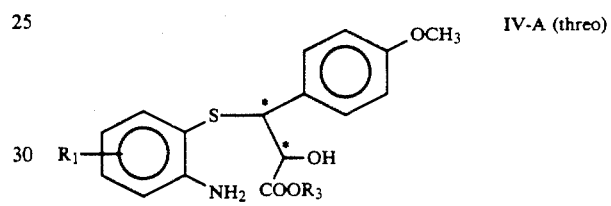

wherein $R_1$ represents a hydrogen or chlorine atom, $R_3$ represents a $C_1-C_3$ alkyl, the asterisks mark the asymmetric carbon atoms; which comprises the treatment of the racemic mixture of compound IV-A with optically active tartaric acid or analogs therof in a suitable solvent, the separation of the diastereoisomeric salts of compound IV-A with optically active tartaric acid or analogs thereof and, if desired, the liberation of the enantiomers of compound IV-A from the salt.

8. A process according to claim 7 in which the suitable solvent is a lower alkanecarboxylic acid optionally in admixture with small amounts of water.

9. A process for the preparation of an enantiomerically pure aminoester of formula

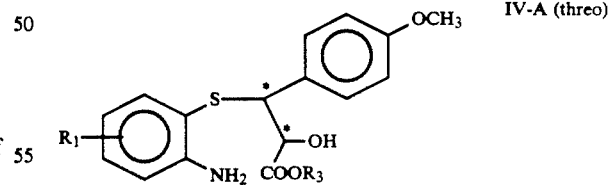

wherein $R_1$ represents a hydrogen or chlorine atom, $R_3$ represents a $C_1-C_3$ alkyl, the asterisks mark the asymmetric carbon atoms; which comprises the crystallization in a suitable solvent of an enantiomeric mixture enriched in the same enantiomer.

10. A process according to claim 9 wherein the suitable solvent is selected among lower alkanecarboxylic acids, lower alcohols and chlorinated hydrocarbons optionally in the presence of small amounts of water.

* * * * *

UNITED STATES PATENT AND TRADEMARK OFFICE
CERTIFICATE OF CORRECTION

PATENT NO.   :  5,144,025
DATED        :  September 1, 1992
INVENTOR(S)  :  Dario TENTORIO It is certified that error appears in the above-identified patent and that said Letters Patent is hereby corrected as shown below:

On the Title Page, Item [30] should read;

-- [30]    Foreign Application Priority Data

April 13, 1989 [IT] Italy ............. 20134 A/89 --

Signed and Sealed this

Twelfth Day of July, 1994

Attest:

BRUCE LEHMAN

*Attesting Officer*          *Commissioner of Patents and Trademarks*